United States Patent [19]

Greene et al.

[11] Patent Number: 4,557,898
[45] Date of Patent: Dec. 10, 1985

[54] METHOD OF DISINFECTING AND STERILIZING WITH HYDROGEN PEROXIDE COMPOSITIONS

[75] Inventors: Donald F. Greene, Middletown; Virginia L. Urban, Midland Park, both of N.J.

[73] Assignee: Sterling Drug Inc., New York, N.Y.

[21] Appl. No.: 704,431

[22] Filed: Feb. 22, 1985

Related U.S. Application Data

[60] Division of Ser. No. 95,947, Nov. 20, 1979, Pat. No. 4,518,585, which is a continuation-in-part of Ser. No. 902,006, May 1, 1978, abandoned.

[30] Foreign Application Priority Data

May 1, 1979 [CA] Canada .................................. 326734

[51] Int. Cl.⁴ ..................... A01N 31/00; A01N 31/14; A01N 59/00; A61L 2/16
[52] U.S. Cl. ..................................... 422/28; 252/106; 424/130; 514/714
[58] Field of Search .......................... 422/28; 424/130; 252/106

[56] References Cited

U.S. PATENT DOCUMENTS

| | | | |
|---|---|---|---|
| 2,030,093 | 2/1936 | Bousquet et al. | 424/325 X |
| 2,489,965 | 11/1949 | Kolloff | 424/325 X |
| 3,574,827 | 4/1971 | Beerbower | 424/358 |
| 3,579,465 | 5/1971 | Schmolka | 424/60 |
| 3,639,574 | 2/1972 | Schmolka | 424/130 |
| 3,678,156 | 7/1972 | MacMillan et al. | 424/66 |
| 3,704,227 | 11/1972 | Hill | 424/130 |
| 3,816,324 | 6/1974 | Fine et al. | 424/130 |
| 3,852,210 | 12/1974 | Krezanoski | 252/95 |
| 4,041,033 | 8/1977 | Douglass | 252/107 |
| 4,169,123 | 9/1979 | Forstrom et al. | 422/28 X |
| 4,169,124 | 9/1979 | Forstrom et al. | 422/28 X |

FOREIGN PATENT DOCUMENTS

| | | | |
|---|---|---|---|
| 2311667 | 9/1974 | Fed. Rep. of Germany | 424/313 |
| 1337858 | 11/1973 | United Kingdom | 424/313 |
| 1492536 | 11/1977 | United Kingdom | 424/313 |

OTHER PUBLICATIONS

Merck Index, Ninth Edition, Monograph 4691.
Lebensmittel Wissenschaft Und Technologie, vol. 5 (1972), No. 6, pp. 221-225.
V. I. Vashkov et al., Chem. Abstracts, 1975, vol. 83, 65443e.
V. I. Vashkov, Chem. Abstracts, 1973, vol. 78, 106128W.
V. Grapmanis et al., Chem. Abstracts, 1974, vol. 81, 21599g.
T. I. Istomina et al., Chem. Abstracts, 1973, vol. 78, 67459k.
J. R. V. De Rezende, Chem. Abstracts, 1972, vol. 76, 144792b.
J. R. V. De Rezende, Chem. Abstracts, 1969, vol. 70, 31672v.

*Primary Examiner*—Dale R. Ore
*Attorney, Agent, or Firm*—Frederik W. Stonner; B. Woodrow Wyatt; Paul E. Dupont

[57] ABSTRACT

Aqueous acidic disinfecting and sterilizing compositions containing hydrogen peroxide, a surfactant and an aqueous alcoholic mixture of a tertiary amine and a fatty acid alkanolamide are non-irritating, have in-use stability and are effective for cold and warm sterilization.

12 Claims, No Drawings

METHOD OF DISINFECTING AND STERILIZING WITH HYDROGEN PEROXIDE COMPOSITIONS

This application is a division of application Ser. No. 95,947, Nov. 20, 1979, now U.S. Pat. No. 4,518,585, which is a continuation-in-part of application Ser. No. 902,006, May 1, 1978, abandoned.

BACKGROUND OF THE INVENTION

1. Field of the Invention

This invention relates to hydrogen peroxide compositions useful for disinfection and sterilization of metal, ceramic and plastic surfaces, especially medical and dental equipment, for example, inhalation therapy equipment, and instruments which cannot be sterilized by steam.

2. Description of the Prior Art

Disinfection refers to destruction of vegetative microorganisms and viruses; sterilization additionally refers to destruction of microbial spores, thus, all microscopic life forms.

The currently used chemical disinfectants and sterilants are ethylene oxide and compositions of aldehydes, especially formaldehyde, and dialdehydes, especially glutaraldehyde.

Ethylene oxide is a gas at ordinary temperatures and pressures and is used in gaseous form. It is an irritant to human tissues. After sterilization long periods of aeration (8 to 24 hours) are required for desorption of residual ethylene oxide from instruments sufficient to avoid irritation by the instruments during reuse.

Glutaraldehyde is used alone or in combination with formaldehyde in the form of aqueous compositions. The aldehydic fumes of the compositions are irritating to the eyes and nose, and in some cases to the skin, of the user. A currently sold and used alkaline glutaraldehyde composition is recommended for cold (20° C.) sterilization but is not recommended for warm (50° C.) sterilization.

Hydrogen peroxide is known to be a potent, non-irritating germicide and has been used for many years as a topical antiseptic (The Merck Index, Ninth Edition, Monograph 4691), especially as a 3 percent aqueous solution (ibid., Monograph 4692), but has not been widely used for disinfection and sterilization due to its instability and its corrosiveness to metal surfaces. The decomposition of hydrogen peroxide to water and oxygen is catalyzed by the enzyme, catalase, which is present in organic matter. Residual organic matter from used medical and dental equipment and instruments, which is contacted with hydrogen peroxide during use of disinfecting and sterilizing compositions thereof, therefore accelerates the decomposition and shortens the time during which the compositions can be reused. Although the stability of hydrogen peroxide is known to be increased by the presence of acids (ibid., Monograph 4691), which are believed to denature and therefore prevent the catalytic effect of the catalase, hydrogen peroxide disinfecting and sterilizing compositions which are sufficiently stable to the presence of organic matter to be practical, i.e., reusable over an extended period of time, are not known.

The present invention therefore satisfies the need for a non-irritating and less corrosive hydrogen peroxide disinfecting and sterilizing composition which is stable against organic matter contamination and maintains full antimicrobial effectiveness on repeated use at ambient and elevated temperatures over an extended period of time.

SUMMARY OF THE INVENTION

In one aspect of the invention there is provided an aqueous disinfecting and sterilizing composition consisting essentially of by weight of the composition
  (a) from about 0.5 to about 50 percent of hydrogen peroxide,
  (b) from about 0.1 to about 30 percent of a surfactant which is compatible with hydrogen peroxide,
  (c) from about 0.1 to about 3 percent of an organic or inorganic acid,
  (d) from 0 to about 1 percent of an organic triazole corrosion inhibitor,
  (e) from about 0.01 to about 1 percent of an aqueous-alcoholic mixture of a tertiary amine and a fatty acid alkanolamide and
  (f) the balance water; said composition having a pH below about 5.

In a second aspect of the invention there is provided a method for disinfecting and sterilizing a surface which comprises treating the surface with an effective amount of the aqueous disinfecting and sterilizing composition defined above.

DETAILED DESCRIPTION OF THE INVENTION INCLUSIVE OF THE PREFERRED EMBODIMENTS

A preferred range of concentration of hydrogen peroxide is from about 0.5 to about 10 percent by weight of the composition. A particularly preferred range of concentration of hydrogen peroxide is from about 6 to about 8 weight-percent, which is achieved by dilution of more concentrated commercially available forms, for example, 30 and 90 percent hydrogen peroxide (The Merck Index, Ninth Edition, Monograph 4693 and 4691). Hydrogen peroxide containing inorganic additives, for example, stabilizers, should be avoided because such additives have been found to interfere with the effectiveness of the compositions.

The composition of the invention should have a pH below about 5, preferably below 3.

The composition of the invention contains from about 0.1 to about 30 weight-percent of a surfactant. Any surfactant which is compatible with hydrogen peroxide in acidic aqueous media, that is, which is relatively stable against oxidation and decomposition in the presence of acidic aqueous hydrogen peroxide, can be employed. Thus surfactants which contain moieties which are oxidizable by acidic aqueous hydrogen peroxide should be avoided. Suitable surfactants can be selected from nonionic, anionic, amphoteric or cationic classes of surfactants which are commercially available and well known in the art.

Examples of suitable nonionic surfactants are as follows. Ethoxylated fatty alcohols containing from 11 to 15 carbon atoms in the alcohol and from 3 to 40 moles of ethylene oxide (Tergitol Nonionics; Union Carbide Corporation), such as isomeric linear secondary alcohols with 11 to 15 carbon atoms and 9 moles of ethylene oxide (Tergitol 15-S-9), and linear primary alcohols with 12 to 15 carbon atoms and 9 moles of ethylene oxide (Tergitol 25-L-9). The block copolymer nonionics such as ethylenediamine-reacted copolymers of polyoxyethylene-polyoxypropylene ("Tetronic ® Series Nonionic Surfactants", BASF Wyandotte Corporation) and ethylene glycol-reacted polyoxyethylene-polyoxypropylene copolymers of the formula [HO(CH$_2$CH$_2$O)$_x$(CHCH$_3$—CH$_2$O)$_y$(CH$_2$CH$_2$O)$_z$H], such as, for example, where x, y and z respectively are 13, 30 and 13 (Pluronic L-64; BASF Wyandotte Corporation). Alkyl phenol ethoxylates such as nonylphenoxypolyethoxyethanol with 9 to 10 moles of ethylene oxide (Triton N-101; Rohm & Haas Co.). Alkanolamides for example, fatty acid alkanolamides having one or two hydroxyethyl or hydroxypropyl groups such as coconut and tallow fatty acid ethanolamide and diethanolamide; and oleic acid diethanolamide. Amine oxides, for example, those derived from tertiary amines having an alkyl group of from eight to twenty carbon atoms and two lower alkyl or alkanol groups of up to four carbon atoms such as dimethyl dodecylamine oxide and di(2-hydroxyethyl)tetradecylamine oxide.

Examples of suitable anionic surfactants are the alkyl sulfate salts, e.g., alkali metal alkyl sulfates, having from 8 to 18 carbon atoms such as sodium lauryl sulfate, the alkyl sulfonate salts, e.g., alkali metal alkyl sulfonates, having from 8 to 22 carbon atoms such as sodium-1-decane sulfonate and sodium 2-tridecane sulfonate, and the alkylaryl sulfonate salts, e.g., alkali metal alkylaryl sulfonates, such as sodium dodecylbenzenesulfonate and disodium 4-dodecylated oxydibenzenesulfonate.

Examples of suitable amphoteric surfactants are as follows. Fatty imidazoline derivatives (MIRANOL ® Amphoteric Surface Active Agents; The Miranol Chemical Company) having the structural formula:

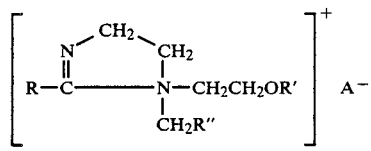

where R is a fatty radical; R' is hydrogen or —CH$_2$COOM; R" is —COOM, —CH$_2$COOM or —CHOHCH$_2$SO$_3$M and A is hydroxyl, chloride, sulfate or surface active sulfate or sulfonate group; where M is sodium, hydrogen or an organic ammonium radical, for example Miranol JEM Conc. where R is a mixture of ⅔ caprylic and ⅓ ethylhexoic acid, R' is —CH$_2$COONa, R" is —COONa and A is hydroxyl. Betaines such as alkyl amide sulfobetaine (Lonzaine CS; Lonza Inc.).

Examples of suitable cationics are polyethoxylated amines and quaternary ammonium compounds such as alkyl dimethyl benzyl ammonium chloride (Cyncal; The Hilton-Davis Chemical Company); a mixture of Cyncal type quaternaries and alkyl dimethyl ethylbenzyl ammonium chloride (BTC 2125M; Onyx Chemical Co.); and dialkyl quaternary ammonia compounds.

Preferred surfactants are the nonionics, particularly ethylenediamine-reacted copolymers of polyoxyethylene and polyoxypropylene which are known stabilizers of hydrogen peroxide. Those having molecular weights in the range of 500 to 4000 and polyoxyethylene contents in the range of about 1 to about 80 percent per mole are useful in the compositions presently described, and the preferred concentration thereof is about 1 percent.

The composition of the invention contains from about 0.1 to about 3 weight-percent of an organic or inorganic acid. Any organic or inorganic acid whose anion does not interfere with effectiveness, or mixture thereof, is useful in the presently described compositions as a stabilizer of hydrogen peroxide, for example, benzenesulfonic acid, trifluoroacetic acid, hydrochloric acid, nitric acid, phosphoric acid or sulfuric acid. Phosphoric acid is preferred, and the preferred concentration thereof is about 0.85 percent.

Since hydrogen peroxide is corrosive to most metals, the composition of the invention should contain an organic triazole corrosion inhibitor if it is to be used for treating materials made of or containing copper, brass, bronze or multi-metals systems. It is to be understood however that when the composition is to be used for treating non-metallic materials, the composition can but need not contain an organic triazole corrosion inhibitor. The organic triazole corrosion inhibitor, if employed in compositions of the invention, is present in a concentration up to about 1 weight-percent. A preferred inhibitor is benzotriazole (The Merck Index, Ninth Edition, Monograph 1119) ("Cobratec, corrosion inhibitors for copper, brass, bronze and multi-metals systems", Sherwin Williams Chemicals, P.O. Box 5638, Cleveland, Ohio), and the preferred concentration thereof in the presently described compositions is about 0.1 weight-percent.

The aqueous alcoholic tertiary amine-fatty acid alkanolamide mixture is both corrosion inhibitor and surfactant. The useful alcohols include the water-miscible alcohols, especially the lower alkanols and mixtures thereof. The preferred alcohol is isopropyl alcohol in amount from about 1 to about 10 percent of the mixture, preferably about 5 percent. The tertiary amines include the water-miscible lower-molecular-weight tertiary monoamines and polyamines and mixtures thereof. The preferred amine is methenamine in amount from about 15 to about 25 percent of the mixture, preferably about 20 percent. The fatty acid alkanolamides are the lower-hydroxyalkyl amides of higher aliphatic saturated and unsaturated fatty acids, especially those of 12 to 18 carbon atoms and mixtures thereof, for example, dodecanoic acid, tetradecanoic acid, hexadecanoic acid and octadecanoic acid. Lower-hydroxyalkyl is, for example, hydroxyethyl or hydroxypropyl. The preferred amount of fatty acid alkanolamide in the mixture is from about 20 to about 30 percent, most preferably about 30 percent. The preferred concentration of the preferred aqueous isopropyl alcoholic methenamine-fatty acid alkanolamide mixture in the presently described compositions is about 0.2 weight-percent.

The invention is illustrated by the following examples without, however, being limited thereto.

EXAMPLE 1

| Ingredient | Percent by Weight |
|---|---|
| Hydrogen peroxide | 7.5 |
| Ethylenediamine reacted polyoxyethylene-polyoxypropylene block copolymer (Tetronic 908) | 1.0 |
| Phosphoric acid | 0.85 |
| Benzotriazole | 0.1 |
| Aqueous isopropyl alcoholic (about 5 percent) methenamine (about 20 percent)-fatty acid alkanolamide (about 30 percent) mixture* | 0.2 |
| Deionized water to total 100% by weight | |
| pH = 1.8 | |

*Acitrol 5101, E. F. Houghton & Company, Philadelphia, Pennsylvania 19133

The composition of Example 1 was tested for germicidal activity, fungicidal activity, virucidal activity, germicidal activity in the presence of organic matter, tuberculocidal activity and sporicidal activity and the tests showed the following results (Test Nos. 1–17):

Test No. 1: Germicidal Activity
Procedure: Use Dilution Method - Official - as described by the Official Methods of Analysis of the Association of Official Analytical Chemists: 62-63, 11th ed., Washington, D.C., 1970.
Dilution Tested: Undiluted

| Test Organism | No. Cylinders + Out of 20 Tested | Phenol Resistance of Culture |
|---|---|---|
| Salmonella choleraesuis ATCC 10708 | 0 | 1:90 |
| Salmonella paratyphi ATCC 9281 | 0 | 1:70 |
| Salmonella schottmuelleri ATCC 10719 | 0 | 1:90 |
| Shigella dysenteriae ATCC 11835 | 0 | 1:60 |
| Enterobacter aerogenes ATCC 13048 | 0 | 1:90 |
| Escherichia coli (AMC 198) ATCC 11229 | 0 | 1:80 |
| Proteus vulgaris ATCC 9920 | 0 | 1:120 |
| Pseudomonas aeruginosa ATCC 15442 | 0 | 1:180 |
| Klebsiella pneumoniae ATCC 9997 | 0 | 1:90 |
| Serratia marcescens ATCC 8195 | 0 | 1:80 |
| Staphylococcus aureus ATCC 6538 | 0 | 1:60 |
| Staphylococcus aureus 80/81 (Penicillin Resistant) | 0 | 1:70 |
| Streptococcus pyogenes ATCC 12384 | 0 | 1:60 |
| Streptococcus faecalis ATCC 828 | 0 | 1:60 |
| Streptococcus salivarius ATCC 9222 | 0 | 1:120 |
| Corynebacterium diphtheriae ATCC 11913 | 0 | 1:100 |
| Candida albicans ATCC 10231 | 0 | 1:70 |
| Trichophyton mentagrophytes ATCC 9533 | 0 | 1:60 |
| Aspergillus niger ATCC 6275 | 0 | 1:90 |

Note: Two subcultures were used for each carrier.

Test No. 2: Germicidal Activity
Procedure: Use Dilution Method - Official - as described by the Official Methods of Analysis of the Association of Official Analytical Chemists: 62-63, Washington, D.C., 1970.
60 Day Shelf Life
No. Cylinders + Out of Each 10 Tested

| Sample | Dilution | Staphylococcus aureus |
|---|---|---|
| 1. | Undiluted | 0 |
| | | 0 |
| | | 0 |
| 2. | Undiluted | 0 |
| | | 0 |
| | | 0 |

| | 5' | 10' | 15' |
|---|---|---|---|
| Phenol 1:60 | + | − | − |
| 1:70 | + | + | + |
| 1:80 | + | + | + |

Note: Two subcultures were used for each carrier.

Test No. 3: Germicidal Activity
Procedure: Use Dilution Method - Official - as described by the Official Methods of Analysis of the Association of Official Analytical Chemists: 62-63, 11th ed., Washington, D.C., 1970.
No. Cylinders + Out of Each 10 Tested

| Sample | Dilution | Pseudomonas aeruginosa |
|---|---|---|
| 1. | Undiluted | 0 |
| | | 0 |
| | | 0 |
| 2. | Undiluted | 0 |
| | | 0 |
| | | 0 |
| 3. | Undiluted | 0 |
| | | 0 |
| | | 0 |

| | 5' | 10' | 15' |
|---|---|---|---|
| Phenol 1:80 | − | − | − |
| 1:90 | + | + | + |
| 1:100 | + | + | + |

Note: Two subcultures were used for each carrier.

Test No. 4: Germicidal Activity
Procedure: Use Dilution Method - Official - as described by the Official Methods of Analysis of the Association of Official Analytical Chemists: 62-63, 11th ed., Washington, D.C., 1970.
No. Cylinders + Out of Each 10 Tested

| Sample | Dilution | Staphylococcus aureus | Salmonella choleraesuis |
|---|---|---|---|
| 1. | Undiluted | 0 | 0 |
| | | 0 | 0 |
| | | 0 | 0 |
| | | 0 | |
| | | 0 | |
| 2. | Undiluted | 0 | 0 |
| | | 0 | 0 |
| | | 0 | 0 |
| | | 0 | |
| | | 0 | |
| 3. | Undiluted | 0 | 0 |
| | | 0 | 0 |
| | | 0 | 0 |
| | | 0 | |
| | | 0 | |

| | 5' | 10' | 15' | | 5' | 10' | 15' |
|---|---|---|---|---|---|---|---|
| Phenol 1:60 | + | − | − | 1:80 | − | − | − |
| 1:70 | + | + | + | 1:90 | + | − | − |
| 1:80 | + | + | + | 1:100 | + | + | + |

Note: Two subcultures were used for each carrier.

Test No. 5: Fungicidal Activity
Procedure: Fungicidal Test - Official - as described by the Official Methods of Analysis of the Association of Official Analytical Chemists: 65-66, 11th ed., Washington, D.C., 1970.

| | | Trichophyton interdigitale | | | | | |
|---|---|---|---|---|---|---|---|
| | | Test No. 1 | | | Test No. 2 | | |
| Dilution | | 5' | 10' | 15' | 5' | 10' | 15' |
| Undiluted | | − | − | − | − | − | − |
| 1:5 | | + | − | − | + | + | − |
| 1:10 | | + | + | + | + | + | + |
| 1:20 | | + | + | − | + | + | + |
| Phenol | 1:45 | − | − | − | − | − | − |
| | 1:60 | + | − | − | + | + | − |
| | 1:70 | + | + | + | + | + | + |

Test No. 6: Germicidal Activity in the Presence of Organic Matter
Procedure: Same as the Use Dilution Method - Official - as described by the Official Methods of Analysis of the Association of Official Analytical Chemists: 62-63, 11th ed., Washington, D.C., 1970.
EXCEPT
The carriers were immersed in 10 ml. of the composition of Example 1 containing 5% horse serum (par. 4.009 - page 62).
No. of Carriers + Out of Each 10 Tested

| Sample | Dilution | S. aureus | | | S. choleraesuis | | | Ps. aeruginosa | | |
|---|---|---|---|---|---|---|---|---|---|---|
| 1. | Undiluted | 0 | | | 0 | | | 0 | | |
| | | 5' | 10' | 15' | 5' | 10' | 15' | 5' | 10' | 15' |
| Phenol | 1:60 | + | − | − | | | | | | |
| | 1:70 | + | + | + | | | | | | |

-continued

| | | | | | | | | | |
|---|---|---|---|---|---|---|---|---|---|
| 1:80 | + | + | + | − | − | − | − | − | − |
| 1:90 | | | | + | − | − | + | + | − |
| 1:100 | | | | + | + | + | + | + | + |

Note: Two subcultures were used for each carrier.

Test No. 7: Tuberculocidal Activity

Procedure: Tuberculocidal Activity - Official - as described by the Official Methods of Analysis of the Association of Official Analytical Chemists: 71–72, 11th ed., Washington, D.C., 1970. *Mycobacterium tuberculosis* var. bovis (BCG)

No. Tubes +

| Sample | Dilution | No. Rings Tested | Proskauer-Beck | Middle-brook | Kirchner |
|---|---|---|---|---|---|
| 1. Phenol | Undiluted | 10 | 0 | 0 | 0 |
| | 1:50 | 10 | 0 | 0 | 0 |
| | 1:75 | 10 | 0 | 8 | 8 |

Note: Two subcultures were used for each carrier.

Test No. 8: Sporicidal Activity

Procedure: Sporicidal Test - Official - as described by the Official Methods of Analysis of the Association of Official Analytical Chemists: 64–65, 11th ed., Washington, D.C., 1970. The exposure time was 6 hours at 20° C. Two subcultures were used for each carrier.

No. of Carriers + Out of Each 10 Tested
*Bacillus subtilis*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| 3. | Undiluted | 0 | 0 |
| | | 0 | 0 |
| | | 0 | 0 |
| Controls | | 3/3+ | 3/3+ |

| | 1' | 2' | 5' | 10' | 1' | 2' | 5' | 10' |
|---|---|---|---|---|---|---|---|---|
| 2.5 N HCl | + | + | − | − | + | + | + | − |

Test No. 9: Sporicidal Activity

Procedure: Sporicidal Test - Official - as described by the Official Methods of Analysis of the Association of Official Analytical Chemists: 64–65, 11th ed., Washington, D.C., 1970. The exposure time was 10 minutes at the elevated temperature of 50° C. Two subcultures were used for each carrier.

No. of Carriers + Out of Each 10 Tested
*Bacillus subtilis*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| 3. | Undiluted | 0 | 0 |
| | | 0 | 0 |
| | | 0 | 0 |
| Controls | | 3/3+ | 3/3+ |

| | 1' | 2' | 5' | 10' | 1' | 2' | 5' | 10' |
|---|---|---|---|---|---|---|---|---|
| 2.5 N HCl | + | + | − | − | + | + | + | − |

Test No. 10: Sporicidal Activity

Procedure: Sporicidal Test - Official - as described by the Official Methods of Analysis of the Association of Official Analytical Chemists: 64–65, 11th ed., Washington, D.C., 1970. The exposure time was 6 hours at 20° C. Two subcultures were used for each carrier.

60 Day Shelf Life
No. of Carriers + Out of Each 10 Tested
*Bacillus subtilis*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| Controls | | 2/2+ | 2/2+ |

| | 1' | 2' | 5' | 10' | 1' | 2' | 5' | 10' |
|---|---|---|---|---|---|---|---|---|
| 2.5 N HCl | + | + | − | − | + | + | + | − |

Test No. 11: Sporicidal Activity

Procedure: Sporicidal Test - Official - as described by the Official Methods of Analysis of the Association of Official Analytical Chemists: 64–65, 11th ed., Washington, D.C., 1970. The exposure time was 10 minutes at the elevated temperature of 50° C. Two subcultures were used for each carrier.

60 Day Shelf Life
No. of Carriers + Out of Each 10 Tested
*Bacillus subtilis*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| Controls | | 2/2+ | 2/2+ |

| | 1' | 2' | 5' | 10' | 1' | 2' | 5' | 10' |
|---|---|---|---|---|---|---|---|---|
| 2.5 N HCl | + | + | − | − | + | + | + | − |

Test No. 12: Sporicidal Activity

Procedure: Sporicidal Test - Official - as described by the Official Methods of Analysis of the Association of Official Analytical Chemists: 64–65, 11th ed., Washington, D.C., 1970. The exposure time was 6 hours at 20° C. Two subcultures were used for each carrier.

No. of Carriers + Out of Each 10 Tested
*Clostridium sporogenes*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| 3. | Undiluted | 0 | 0 |
| | | 0 | 0 |
| | | 0 | 0 |
| Controls | | 3/3+ | 3/3+ |

| | 5' | 10' | 20' | 30' | 5' | 10' | 20' | 30' |
|---|---|---|---|---|---|---|---|---|
| 2.5 N HCl | + | + | − | − | + | + | + | − |

Test No. 13: Sporicidal Activity

Procedure: Sporicidal Test - Official - as described by the Official Methods of Analysis of the Association of Official Analytical Chemists: 64–65, 11th ed., Washington, D.C., 1970. The exposure time was 10 minutes at the elevated temperature of 50° C. Two subcultures were used for each carrier.

No. of Carriers + Out of Each 10 Tested
*Clostridium sporogenes*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| 3. | Undiluted | 0 | 0 |
| | | 0 | 0 |
| | | 0 | 0 |
| Controls | | 3/3+ | 3/3+ |

| | 5' | 10' | 20' | 30' | 5' | 10' | 20' | 30' |

-continued

| | | 5' | 10' | 20' | 30' | 5' | 10' | 20' | 30' |
|---|---|---|---|---|---|---|---|---|---|
| 2.5 N HCl | | + | + | − | − | + | + | + | − |

Test No. 14: Sporicidal Activity

Procedure: Sporicidal Test - Official - as described by the Official Methods of Analysis of the Association of Official Analytical Chemists: 64–65, 11th ed., Washington, D.C., 1970. The exposure time was 6 hours at 20° C. Two subcultures were used for each carrier.

60 Day Shelf Life
No. of Carriers + Out of Each 10 Tested
*Clostridium sporogenes*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| Controls | | 2/2+ | 2/2+ |

| | | 5' | 10' | 20' | 30' | 5' | 10' | 20' | 30' |
|---|---|---|---|---|---|---|---|---|---|
| 2.5 N HCl | | + | + | − | − | + | + | + | − |

Test No. 15: Sporicidal Activity

Procedure: Sporicidal Test - Official - as described by the Official Methods of Analysis of the Association of Official Analytical Chemists: 64–65, 11th ed., Washington, D.C., 1970. The exposure time was 10 minutes at the elevated temperature of 50° C. Two subcultures were used for each carrier.

60 Day Shelf Life
No. of Carriers + Out of Each 10 Tested
*Clostridium sporogenes*

| Sample | Dilution | Porcelain Cylinders | Suture Loops |
|---|---|---|---|
| 1. | Undiluted | 0 | 0 |
| | | 0 | 0 |
| | | 0 | 0 |
| 2. | Undiluted | 0 | 0 |
| | | 0 | 0 |
| | | 0 | 0 |
| Controls | | 2/2+ | 2/2+ |

| | | 5' | 10' | 20' | 30' | 5' | 10' | 20' | 30' |
|---|---|---|---|---|---|---|---|---|---|
| 2.5 N HCl | | + | + | − | − | + | + | + | − |

Test No. 16: Sporicidal Activity - *C. tetani*

Procedure: Sporicidal Test - Official - as described by the Official Methods of Analysis of the Association of Official Analytical Chemists: 64–65, 11th ed., Washington, D.C., 1975.
Test Organism: *Clostridium tetani*, ATCC 19406
Exposure Times: (1) 6 hours at 20° C.
(2) 10 minutes at 50° C.
Type of Carriers: Porcelain cylinders

| Sample | Test Dilution | Contact Time | No. of Carriers + Out of Each 10 Tested | |
|---|---|---|---|---|
| | | | 1st Subculture | 2nd Subculture |
| 1. | Undiluted | 6 hours 20° C. | 0 | 0 |
| | | | 0 | 0 |
| | | | 0 | 0 |
| | | 10 minutes 50° C. | 0 | 0 |
| | | | 0 | 0 |
| | | | .0 | 0 |
| Controls | | | 3/3+ | 3/3+ |

| | 2' | 5' | 10' | 20' |
|---|---|---|---|---|
| 2.5 N HCl | + | + | − | − |

TEST NO. 17—VIRUCIDAL ACTIVITY

Procedure:

EPA APPROVED VIRUCIDAL SUSPENSION AND HARD SURFACE TEST METHODS. The number of tests shown is that required for registration with the EPA as described by Stuart, L.S., Testing Sterilizers, Disinfectants Sanitizers And Bacteriostatic Chemicals, C.S.M.A. Proceedings: pages 123–125, May, 1969.

Suspension Test Method

The virus was grown and assayed in the appropriate host.

For the test, 1 ml. of virus was added to 9 ml. of the germicide. After 10 minutes contact at room temperature the virus-germicide mixture was diluted in broth to the titer of the virus and inactivation was determined by comparing the titer of the treated virus with that of the untreated virus. Viral Controls. Saline was substituted for the germicide. The presence of active virus was determined by the inoculation of 0.1 ml. of the test preparation into the host. The hosts were incubated and observed for cytopathogenic effect.

Hard Surface Test Method

The virus was grown and assayed in the appropriate host.

One-tenth ml. of virus is spread over the surface of ten glass slides and allowed to dry. As soon as material is dried, 0.2 ml. of water is placed over five slides as controls. To test for viral inactivation, 0.2 ml. of the test germicide is placed on five slides containing dried virus. After 10 minutes contact at room temperature, the fluid from the control and the test germicide slides is removed with a pasteur pipette and added to 2 ml. of trypticase soy broth as a diluent. A sterile swab is used to remove residual virus by a 3 time interval dipping into the broth diluent. Serial ten-fold dilutions to the titer of the virus are then made. Germicide controls are prepared by adding 0.2 ml. of the test germicide to five slides, fluid removed, and ten-fold serial dilutions prepared as described above.

To detect presence or absence of live virus, one-tenth ml. of each broth dilution is inoculated into the host and incubated. After incubation, controls are observed for cytopathogenic effect to the titer of virus and degree of inactiviation determined for germicide treated virus.

The exposure time was 10 minutes at room temperature.

The results are tabulated in Table I below.

TABLE I

| Test | Test Virus | Titer | Host Grown In | Results* |
|---|---|---|---|---|
| Suspension | Rhinovirus Type 17 | $10^5$ TCID | HeLa Cells | complete inactivation |
| | Rhinovirus Type 39 | $10^6$ TCID | WI-38 | complete inactivation |
| | Herpes simplex | $10^6$ TCID | Rabbit Kidney Cells | complete inactivation |
| | Influenza A$_2$ (England) | $10^7$ TCID | Chick embryo | complete inactivation |
| | Adenovirus Type 5 | $10^6$ TCID | HeLa Cells | complete inactivation |
| Hard Surface | Rhinovirus Type 17 | $10^7$ TCID | HeLa Cells | complete inactivation |
| | Poliovirus Type 1 | $10^7$ TCID | HeLa Cells | complete inactivation |
| | Influenza A$_2$ (England) | $10^7$ TCID | Chick embryo | complete inactivation |
| | Adenovirus Type 2 | $10^6$ TCID | HeLa Cells | complete inactivation |

*Results: Complete inactivation indicates at least 3 logs of virus were inactivated with no residual virus detected within limits allowed by the toxicity of germicide.

The composition of Example 1 showed the following antimicrobial efficacy:

| Activity | Immersion Time | Temperature (°C.) |
| --- | --- | --- |
| Sterilization | 6 hours | 20 |
| Sterilization | 10 minutes | 50 |
| Bactericidal | 10 minutes | 20 |
| Fungicidal | 10 minutes | 20 |
| Virucidal | 10 minutes | 20 |
| Tuberculocidal | 10 minutes | 20 |

The advantage of the presently described and claimed compositions as illustrated by the foregoing efficacy is shown by the following comparative efficacies of prior art disinfectants and sterilants.

| Acidic Glutaraldehyde | | |
| --- | --- | --- |
| Activity | Immersion Time | Temperature (°C.) |
| Sterilization | 1 hour | 60 |
| Bactericidal | 10 minutes | 20 |
| Tuberculocidal | 20 minutes | 20 |
| Alkaline Glutaraldehyde | | |
| Activity | Immersion Time | Temperature (°C.) |
| Sterilization | 10 hours | 20 |
| Disinfection | 10 minutes | 20 |
| Formaldehyde | | |
| Activity | Immersion Time | Temperature (°C.) |
| Sterilization | 18 hours | 20 |
| Disinfection | 10 minutes | 20 |

Sterilization with ethylene oxide requires contact times ranging from 2.5 to 24 hours.

The composition of Example 1 was examined for germicidal and sporicidal activities in a simulated in-use test using the following procedure:

Two large plastic containers were filled with 5000 ml. of the composition. To each approximately 15 hospital instruments commonly sterilized by a cold sterilizing procedure was added (scissors, scalpel blades, inhalation therapy apparatus, hoses, nozzles, etc.). To one of the containers 2% sterile horse serum was added at the start of the test and an additional 2% was added after 3 weeks. The containers were loosely covered and stored in the dark at room temperature. Each container was inoculated on a daily basis with 50 cylinders contaminated with the following test organisms:

Salmonella choleraesuis—10 stainless steel rings
Staphylococcus aureus—10 stainless steel rings
Pseudomonas aeruginosa—10 stainless steel rings
Bacillus subtilis—10 porcelain rings
Clostridium sporogenes—10 porcelain rings No inoculations were carried out on the test days. After designated time intervals (1, 2, 3, 4 and 6 weeks), 400 ml. aliquots were taken from each container and tested for germicidal efficacy by the official A.O.A.C. Use Dilution Test against the organisms S. choleraesuis, S. aureus, and Ps. aeruginosa, and for sporicidal activity (6 hour exposure) by the official A.O.A.C. Sporicidal Test against the spores of the organisms B. subtilis and C. sporogenes.

The results, tabulated in Table II below, indicate that the germicidal and sporicidal activities of the composition of Example 1 were maintained for at least six weeks under normal use conditions, even in the presence of a heavy organic load.

TABLE II

| Sample | Storage time | No. Stainless Steel Carriers ⊕ per 10 tested | | | No. Porcelain Carriers ⊕ per 10 tested | |
| --- | --- | --- | --- | --- | --- | --- |
| | | S. choleraesuis | S. aureus | Ps. aeruginosa | B. subtilis | Cl. sporogenes |
| Composition of Example 1 | 1 week | 0 | 0 | 0 | 0 | 0 |
| | 2 weeks | 0 | 0 | 0 | 0 | 0 |
| | 3 weeks | 0 | 0 | 0 | 0 | 0 |
| | 4 weeks | 0 | 0 | 0 | 0 | 0 |
| | 6 weeks | 0 | 0 | 0 | 0 | 0 |
| Composition of Example 1 with horse serum[1] | 1 week | 0 | 0 | 0 | 0 | 0 |
| | 2 weeks | 0 | 0 | 0 | 0 | 0 |
| | 3 weeks | 0 | 0 | 0 | 0 | 0 |
| | 4 weeks | 0 | 0 | 0 | 0 | 0 |
| | 6 weeks | 0 | 0 | 0 | 0 | 0 |

[1] 2% horse serum was added at time zero and an additional 2% was added at time 3 weeks.
Note: Double subcultures were used for all cylinders; the first subculture tubes contained 0.05% catalase.

The composition of Example 1 was examined for germicidal, sporicidal, tuberculocidal and fungicidal activities in a simulated in-use test using the following procedures:

Two large plastic containers were filled with 10,000 ml. of the composition. To each of the containers, approximately 15 hospital instruments commonly sterilized by a chemical sterilizing procedure (scissors, scalpel blades, inhalation therapy apparatus: hoses, nozzles, etc.) were added. To one of the containers 2% sterile horse serum was added at the start of the test (time zero). After 3 weeks (T-3 weeks) an additional 2% sterile horse serum was added to the same container (resulting in 96% composition and a total of 4% horse serum). All containers were loosely covered and stored on alternate days at room temperature and 50° C., e.g. Day 1-room temperature, Day 2–50° C., Day 3-room temperature, Day 4–50° C., etc., except on weekends when the containers were stored at room temperature.

At the start of the test (time zero), microbial challenges were performed via carriers contaminated as per AOAC procedures as follows:

| Time zero | T. interdigitale | 10 stainless steel rings |
| --- | --- | --- |
| Day 1 | M. tuberculosis | 10 porcelain cylinders |
| Day 2–5 | S. choleraesuis | 10 stainless steel rings |
| | S. aureus | 10 stainless steel rings |
| | Ps. aeruginosa | 10 stainless steel rings |
| | B. subtilis | 10 porcelain cylinders |
| | C. sporogenes | 10 porcelain cylinders |
| | C. tetani | 10 porcelain cylinders |

No challenges were made on the weekends or on test days. Testing was conducted after T-1, 2, 3, 4 and 6 weeks.

Therefore, at T-1, 2, 3, 4 and 6 weeks the testing/inoculation schedule was as follows:

| | | |
|---|---|---|
| Day 1 | (Test Day) | |
| Day 2 | T. interdigitale | 10 stainless steel rings |
| | M. tuberculosis | 10 porcelain cylinders |
| Day 3-5 | S. choleraesuis | 10 stainless steel rings |
| | S. aureus | 10 stainless steel rings |
| | Ps. aeruginosa | 10 stainless steel rings |
| | B. subtilis | 10 porcelain cylinders |
| | C. sporogenes | 10 porcelain cylinders |
| | C. tetani | 10 porcelain cylinders |

After T-4 weeks (actually the 5th week) inoculations were similar to T-0 (1st week).

After the following time intervals, T-1 week, T-2 weeks, T-3 weeks, T-4 weeks and T-6 weeks, appropriate aliquots were removed from each container and evaluated for antimicrobial efficacy by the following procedures:

1. Fungicidal Efficacy—AOAC Fungicidal Test vs. T. interdigitale—one (1) test.
2. Sporicidal Activity—AOAC Sporicidal Test (10 minute exposure at 50° C.) vs. B. subtilis, C. sporogenes, C. tetani; 10 porcelain cylinders, 10 suture loops each organism.
3. Tuberculocidal Activity—AOAC Tuberculocidal Test vs. M. tuberculosis var. bovis (BCG) 10 porcelain cylinders.

Additionally, after T-6 weeks appropriate aliquots were removed from each container and evaluated for antimicrobial efficacy by the following procedures and against the following organisms:

1. Germicidal Efficacy—AOAC Use Dilution Test, 10 stainless steel rings each vs.
   a. *Salmonella choleraesuis* ATCC 10708
   b. *Salmonella paratyphi* ATCC 9281
   c. *Salmonella schottmuelleri* ATCC 10719
   d. *Shigella dysenteriae* ATCC 11835
   e. *Enterobacter aerogenes* ATCC 13048
   f. *Escherichia coli* (AMC 198) ATCC 11229
   g. *Proteus vulgaris* ATCC 9920
   h. *Pseudomonas aeruginosa* ATCC 15442
   i. *Klebsiella pneumoniae* ATCC 9997
   j. *Neisseria elongata* ATCC 25295
   k. *Serratia marcescens* ATCC 8195
   l. *Staphylococcus aureus* ATCC 6538
   m. *Staphylococcus aureus* 80/81 (Penicillin Resistant)
   n. *Streptococcus faecalis* ATCC 828
   o. *Streptococcus pyogenes* ATCC 12384
   p. *Streptococcus salivarius* ATCC 9222
   q. *Corynebacterium diphtheriae* ATCC 11913
   r. *Candida albicans* ATCC 10231
   s. *Aspergillus niger* ATCC 6275
   t. *Acinetobacter calcoaceticus* ATCC 9955
   u. *Pseudomonas cepacia* ATCC 25608
   v. *Proteus mirabilis* ATCC 25933
   w. *Trichophyton mentagrophytes* ATCC 9533
2. Sporicidal Activity—AOAC Sporicidal Test (6 hour exposure at 20° C.) vs. B. subtilis, C. sporogenes, C. tetani; 10 porcelain cylinders, 10 suture loops each organism.

Additionally, during the 5th week of testing, the contaminated cylinders used to challenge each of the containers during this week were removed from each of the containers and subcultured into appropriate subculture media after the recommended germicidal exposure times for each organism as follows:

1. Day 1—subcultured the 10 T. interdigitale rings to AOAC fungicidal broth after 10 minutes exposure at room temperature.
2. Day 1—subcultured 10 M. tuberculosis rings to AOAC Tb broths (Middlebrook, Kir P-B) after 10 minutes exposure at room temperature.
3. Day 5—subcultured 10 each S. choleraesuis, S. aureus, Ps. aeruginosa rings to AOAC Letheen Broth after 10 minutes exposure at room temperature.
4. Days 4 and 5—subcultured 10 each B. subtilis, C. sporogenes, C. tetani cylinders to AOAC Thioglycollate broth after:
   a. 6 hours at room temperature (Day 5)
   b. 10 minutes at 50° C. (Day 4)

When the composition of Example 1 was tested in accordance with the above-described simulated in-use test procedures, no test organisms survived in any of the tests. These results indicate that the composition of Example 1 maintains effective germicidal, sporicidal (both 6 hours at room temperature and 10 minutes at 50° C.), tuberculocidal, and fungicidal activity for at least 6 weeks, even in the presence of a high organic load (4% horse serum).

Compositions were prepared (Examples 2 to 6) corresponding exactly to the composition of Example 1 except that the 1% of the ethylenediamine reacted polyoxyethylene-polyoxypropylene surfactant was replaced by 1% of the following surfactants:

| Example | Surfactant | pH |
|---|---|---|
| 2 | Tergitol 25-L-9 | 1.9 |
| 3 | Tergitol 15-S-9 | 2.0 |
| 4 | Miranol Jem | 2.7 |
| 5 | Triton N-101 | 0.85 |
| 6 | Pluronic L-64 | 1.9 |

A composition was prepared (Example 7) corresponding exactly to the composition of Example 1 except that the benzotriazole was omitted. This composition had pH 1.9.

A composition was prepared (Example 8) corresponding exactly to the composition of Example 1 except that the concentration of benzotriazole was increased to 0.5 percent by weight. This composition had pH 2.2.

The compositions of Examples 2 to 8 were examined for sporicidal activity against *Clostridium sporogenes* ATCC 3584 at ten minutes at 50° C. and six hours at 20° C. The procedure used was the A.O.A.C. Sporicidal Test: *Official Methods of Analysis of The Association of Analytical Chemists*, 12 ed., 1975, Washington, D.C., pp. 61-63. The results, tabulated in Table III below, show that the compositions of Examples 2 to 8 are effective sporicides.

TABLE III

| Sample | Test Dilution | Contact Time | No. of porcelain cylinders ⊕ out of 30 Tested C. sporogenes ATCC No. 3584 | |
|---|---|---|---|---|
| | | | 1st subculture[1] | 2nd subculture[1] |
| Example 2 | Undiluted | 10 min/50° C. | 0 | 0 |
| | | 6 hr/20° C. | 0 | 0 |
| Example 3 | Undiluted | 10 min/50° C. | 0 | 0 |
| | | 6 hr/20° C. | 0 | 0 |
| Example 4 | Undiluted | 10 min/50° C. | 0 | 0 |
| | | 6 hr/20° C. | 0 | 0 |

TABLE III-continued

| Sample | Test Dilution | Contact Time | No. of porcelain cylinders ⊕ out of 30 Tested C. sporogenes ATCC No. 3584 | |
|---|---|---|---|---|
| | | | 1st subculture[1] | 2nd subculture[1] |
| Example 5 | Undiluted | 10 min/50° C. | 0 | 0 |
| | | 6 hr/20° C. | 0 | 0 |
| Example 6 | Undiluted | 10 min/50° C. | 0 | 0 |
| | | 6 hr/20° C. | 0 | 0 |
| Example 7 | Undiluted | 10 min/50° C. | 0 | 0 |
| | | 6 hr/20° C. | 0 | 0 |
| Example 8 | Undiluted | 10 min/50° C. | 0 | 0 |
| | | 6 hr/20° C. | 0 | 0 |
| Control of Test Organism | | | | |
| Clostridium sporogenes | | viability 2+/2 | 2.5 N | HCl |
| | | | 2[1]   5[1] | 10[1]   20[1] |
| | | | +      +   | −       −    |

[1]Double subculture tubes were used for all cylinders, 0.005% catalase was added to the first subculture tube.

Six compositions were prepared corresponding exactly to the composition of Example 1 except that the concentration of hydrogen peroxide was varied as follows:

| Example No. | $H_2O_2$ (Weight-Percent) |
|---|---|
| 9 | 5 |
| 10 | 4 |
| 11 | 3 |
| 12 | 2 |
| 13 | 1 |
| 14 | 0.5 |

The compositions of Examples 9 to 14 were found to have effective sporicidal activity when tested in accordance with the test procedure described by the *Official Methods of Analysis of the Association of Official Analytical Chemists:* 64–65, 11th ed., Washington, D.C., 1970. Double subcultures were used for all tests. The results obtained in the test procedure were as follows:

| Composition | No. Porcelain Cylinders + Per 10 Tested | |
|---|---|---|
| | C. sporogenes | B. subtilis |
| Example 9 | 0,0 | — |
| Example 10 | 0,0 | — |
| Example 11 | 0,0 | — |
| Example 12 | 0,0 | — |
| Example 13 | 0,0 | — |
| Example 14 | 0,0,0 | 1,0,0 |

The novel compositions are useful for disinfecting and sterilizing surfaces, both animate and inanimate, contaminated with bacterial, fungal and viral microorganisms and microbial spores in medical and non-medical situations.

The novel compositions are particularly useful in the medical field, i.e., in human and veterinary medicine and surgery and in dentistry, for sterilization and disinfection of a variety of objects made of or containing metal, plastic, rubber and ceramics. Exemplary of such objects are instruments, devices and equipment such as lensed instruments, fiberoptic devices, anesthesia equipment, inhalation equipment, catheters, scalpels, scissors, forceps, needles, syringes, clamps and thermometers. Such objects can be treated with the novel compositions at room and elevated temperatures without adverse effects, i.e., without softening of rubber or plastic or corrosion of metal. However, as noted hereinbefore, when the object to be treated is made of metal, a corrosion inhibitor should be included in the composition.

The novel compositions can also be used for disinfecting or sterilizing surfaces in industrial, domestic and medical environments. For example, in a hospital environment they can be used to disinfect or sterilize walls, floors and work surfaces as well as utensils such as bedpans, urinals, etc.

The novel compositions are also useful for disinfecting or sterilizing skin (antisepsis), for example, in the pre-surgical preparation of skin areas in human and veterinary medicine. For such purposes, preferably low concentrations of hydrogen peroxide should be employed, i.e., concentrations up to about 3 weight-percent.

In use, the novel compositions are generally used at full strength although for any particular purpose they can be diluted. The material to be disinfected or sterilized with the novel composition can be treated by any of the conventional methods which are well known to the art. For example, the material to be disinfected or sterilized can be contacted with the novel compositions by immersion, spraying, swabbing, etc.

A preferred method for treating objects used in the medical field with the novel compositions is by immersion. In such cases the novel compositions can be used at room and elevated temperatures, preferably from about 20° C. to about 50° C. The immersion time required to effect sterilization or disinfection is temperature dependent, progressively less time being required as the temperature is increased. For example, it has been found that when a composition in accordance with this invention having a concentration of hydrogen peroxide of about 7 weight-percent is employed, sterilization and disinfection are effected respectively in 10 minutes and in six hours at 20° C.; and sterilization is effected in 10 minutes at 50° C. The ability of the novel compositions to effect sterilization in as little as 10 minutes at elevated temperatures has significance in the medical and dental fields where a short turnabout time in instrument and equipment use is a distinct advantage.

The novel compositions have unique stability in the presence of organic matter contamination and can be effectively reused for at least six weeks for sterilizing and disinfecting medical and dental equipment, instruments and devices.

We claim:

1. A method for disinfecting and sterilizing a surface which comprises treating the surface with an effective amount of an aqueous disinfecting and sterilizing composition consisting essentially of by weight of the composition:
   (a) from about 0.5 to about 50 percent of hydrogen peroxide,
   (b) from about 0.1 to about 30 percent of a surfactant which is compatible with hydrogen peroxide,
   (c) from about 0.1 to about 3 percent of an organic or inorganic acid,
   (d) from 0 to about 1 percent of an organic triazole corrosion inhibitor,
   (e) from about 0.01 to about 1 percent of an aqueous-alcoholic mixture of a tertiary amine and a fatty acid alkanolamide, and
   (f) the balance water;
   said composition having a pH below about 5.

2. A method according to claim 1 wherein the surfactant is selected from the group consisting of ethoxylated fatty alcohols containing from 11 to 15 carbon atoms in the alcohol and from 3 to 40 moles of ethylene oxide, ethylenediamine-reacted block copolymers of polyoxyethylene-polyoxypropylene, ethylene glycol-reacted polyoxyethylene-polyoxypropylene copolymers, alkyl phenol ethoxylates, and fatty imidazoline derivatives.

3. A method according to claim 2 wherein the corrosion inhibitor is benzotriazole.

4. A method according to claim 3 wherein the acid is phosphoric acid.

5. A method according to claim 4 wherein in the aqueous-alcoholic mixture of a tertiary amine and fatty acid alkanolamide, the alcohol is isopropyl alcohol in amount about 5 percent of the mixture, the tertiary amine is methenamine in amount about 20 percent of the mixture and the fatty acid alkanolamide is in amount about 20 to about 30 percent of the mixture.

6. A method according to claim 5 wherein the hydrogen peroxide concentration is from about 0.5 to about 7.5 percent.

7. A method according to claim 6 wherein
   (a) the hydrogen peroxide concentration is about 7.5 percent,
   (b) the surfactant concentration is about 1 percent,
   (c) the phosphoric acid concentration is about 0.85 percent,
   (d) the benzotriazole concentration is from 0 to about 0.1 percent, and
   (e) the aqueous-isopropyl alcoholic methenamine-fatty acid alkanolamide mixture concentration is about 0.2 percent; and the pH is below about 3.

8. A method according to claim 2 wherein the surfactant is an ethylenediamine-reacted block copolymer of polyoxyethylene-polyoxypropylene.

9. A method according to claim 8 wherein the acid is phosphoric acid and the corrosion inhibitor is benzotriazole.

10. A method according to claim 9 wherein in the aqueous-alcoholic mixture of a tertiary amine and a fatty acid alkanolamide the alcohol is isopropyl alcohol in amount about 5 percent of the mixture, the tertiary amine is methenamine in amount about 20 percent of the mixture and the fatty acid alkanolamide is in amount about 20 to about 30 percent of the mixture.

11. A method according to claim 10 wherein the hydrogen peroxide concentration is from about 0.5 to about 7.5 percent.

12. A method according to claim 11 wherein
   (a) the hydrogen peroxide concentration is about 7.5 percent,
   (b) the concentration of the ethylenediamine-reacted block copolymer of polyoxyethylene-polyoxypropylene is about 1 percent,
   (c) the phosphoric acid concentration is about 0.85 percent,
   (d) the benzotriazole concentration is about 0.1 percent, and
   (e) the aqueous-isopropyl alcoholic methenamine-fatty acid alkanolamide mixture concentration is about 0.2 percent.

* * * * *